(12) United States Patent
Abedi

(10) Patent No.: US 7,393,962 B2
(45) Date of Patent: Jul. 1, 2008

(54) CHEMICAL PROCESS

(75) Inventor: Vahak Abedi, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 88 days.

(21) Appl. No.: 10/599,463

(22) PCT Filed: Mar. 29, 2005

(86) PCT No.: PCT/GB2005/001200

§ 371 (c)(1),
(2), (4) Date: Sep. 29, 2006

(87) PCT Pub. No.: WO2005/095377

PCT Pub. Date: Oct. 13, 2005

(65) Prior Publication Data

US 2007/0197805 A1 Aug. 23, 2007

(30) Foreign Application Priority Data

Mar. 31, 2004 (SE) .................................... 0400873

(51) Int. Cl.
*C07D 317/44* (2006.01)

(52) U.S. Cl. ........................................................ 549/438
(58) Field of Classification Search .................. 549/438
See application file for complete search history.

(56) References Cited

FOREIGN PATENT DOCUMENTS

WO 00/34283 6/2000
WO 01/92263 12/2001

*Primary Examiner*—D. Margaret Seaman
*Assistant Examiner*—Nizal S Chandrakumar
(74) *Attorney, Agent, or Firm*—Pepper Hamilton LLP

(57) ABSTRACT

The present invention provides a process for the preparation of a compound of formula (I): wherein $R^1$ is $C_{1-6}$ alkyl; $R^2$ and $R^3$ are, independently, $C_{1-6}$ alkyl; and $R^4$ is $C_{1-6}$ alkyl or benzyl (wherein the phenyl ring of benzyl is optionally substituted by nitro, $S(O)_2(C_{1-4}$ alkyl), cyano, $C_{1-4}$ alkyl, $C_{1-4}$ alkoxy, $C(O)(C_{1-4}$ alkyl), $N(C_{1-6}$ alkyl$)_2$, $CF_3$ or $OCF_3$); the process comprising reacting a compound of formula (II): wherein $R^2$, $R^3$ and $R^4$ are as defined above, with a suitable base; and reacting the product so formed with $R^1OC(O)CH_2X$, wherein $R^1$ is as defined above and X is chloro, bromo or iodo; wherein the process is carried out in a suitable solvent at a temperature in the range $-40°$ C. to $-5°$ C.; and wherein at least 0.2 moles of the compound of formula (II) are used in the process.

20 Claims, No Drawings

CHEMICAL PROCESS

CROSS-REFERENCE TO RELATED APPLICATIONS

This application is the U.S. National Stage filing of International Application Serial No. PCT/GB2005/001200 filed Mar. 29, 2005, which claims priority to Swedish Application Serial No. 0400873-6 filed Mar. 31, 2004, each of which is incorporated herein by reference in its entirety.

The present invention concerns a process for the preparation of alkoxycarbonylmethoxy cyclopentanes which are useful intermediates in the preparation of pharmaceutically active triazolo[4,5-d]pyrimidine cyclopentanes.

The compound [1S-(1α,2α,3β(1S*,2R*),5β)]-3-[7-[2-(3,4-difluorophenyl)cyclopropyl]amino]-5-(propylthio)-3H-1,2,3-triazolo[4,5-d]pyrimidin-3-yl)-5-(2-hydroxyethoxy)-cyclopentane-1,2-diol (Compound A), and similar such compounds, are disclosed in WO 00/34283 and WO 99/05143. These compounds are disclosed as $P_{2T}$ (which is now usually referred to as $P_2Y_{12}$) receptor antagonists. Such antagonists can be used as, inter alia, inhibitors of platelet activation, aggregation or degranulation.

Compounds of formula (I) (see below) are useful in the preparation of Compound A (see example 1 of WO 01/92263). The preparation of a compound of formula (I) is disclosed in example 1 of WO 01/92263 and in that example the process was conducted at 0° C. It has been found that when scaling up the process of example 1 of WO 01/92263 (say to more than 0.2 mole scale) and keeping the temperature at 0° C., competing side-reactions lead to a significant increase in the level of impurities, an increase in the reagent requirement, and a resulting reduction in the percentage yield of compound of formula (I). This is clearly a problem as it makes the process more costly and less efficient. We have now unexpectedly found that when the process is operated on a 0.2 mole scale or more, the use of a lower temperature allows the compound of formula (I) to be produced in good yield and minimizes the products of the unwanted side reactions.

The present invention provides a process for the preparation of a compound of formula (I):

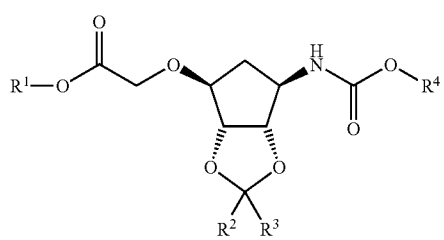

(I)

wherein $R^1$ is $C_{1-6}$ alkyl; $R^2$ and $R^3$ are, independently, $C_{1-6}$ alkyl; and $R^4$ is $C_{1-6}$ alkyl (such as tert-butyl) or benzyl (wherein the phenyl ring of benzyl is optionally substituted by nitro, $S(O)_2(C_{1-4}$ alkyl), cyano, $C_{1-4}$ alkyl, $C_{1-4}$ alkoxy, $C(O)(C_{1-4}$ alkyl), $N(C_{1-6}$ alkyl)$_2$, $CF_3$ or $OCF_3$); the process comprising reacting a compound of formula (II):

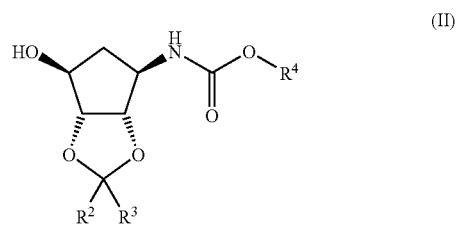

(II)

wherein $R^2$, $R^3$ and $R^4$ are as defined above, with a suitable base; and reacting the product so formed with $R^1OC(O)CH_2X$, wherein $R^1$ is as defined above and X is chloro, bromo or iodo; wherein the process is carried out in a suitable solvent at a temperature in the range −40° C. to −5° C.; and wherein at least 0.2 moles of the compound of formula (II) are used in the process.

Alkyl groups and moieties are straight or branched chain and comprise, for example, 1 to 6 (such as 1 to 4) carbon atoms. Examples of alkyl groups are methyl, ethyl, n-propyl, iso propyl or tert-butyl.

In one particular aspect the present invention provides a process wherein $R^1$ is $C_{1-4}$ alkyl (for example ethyl).

In another aspect the present invention provides a process wherein $R^2$ and $R^3$ are, independently, $C_{1-4}$ alkyl; for example $R^2$ and $R^3$ are both methyl.

In a further aspect of the invention $R^4$ is benzyl (wherein the phenyl ring of benzyl is optionally substituted by $C_{1-4}$ alkyl); for example $R^4$ is unsubstituted benzyl.

In a still further aspect the present invention provides a process wherein X is bromo.

Suitable bases include an alkali metal $C_{1-6}$ alkoxide (for example potassium tert-butoxide).

In another aspect of the invention the molar ratio of suitable base: $R^1O_2CCH_2X$: compound of formula (II) is (1 to 1.3):(1 to 1.3):1, for example (1.1 to 1.3):(1.1 to 1.3):1, such as about 1.2:1.2:1.

Suitable solvents include cyclic and aliphatic ethers (such as tetrahydrofuran, diethyl ether, diisopropyl ether or methyl tert-butyl ether) and aromatic solvents (such as benzene, toluene or a xylene). The solvent can be a mixture of two or more solvents (for example a mixture of an ether and an aromatic solvent, as exemplified above). In another aspect the invention provides a process wherein an ether, as exemplified above, is used as solvent.

In yet another aspect of the invention the temperature is in the range −30° C. to −10° C., for example −25° C. to −15° C.

In a further aspect the process of the present invention comprises adding a solution of suitable base to a solution of a compound of formula (II) at −15 to −25° C., and then adding to this mixture a solution of $R^1OC(O)CH_2X$ at −15 to −25° C., a suitable ether being used as solvent.

A compound of formula (II) can be prepared by a method, or a method analogous to a method, disclosed in the literature (for example WO 01/92263).

The following Example illustrates the invention.

EXAMPLE 1

This Example illustrates a process for the preparation of [3aS-(3aα,4α,6α,6aα)]-[2,2-dimethyl-6-((ethoxycarbonyl)methoxy)-tetrahydro-4H-cyclopenta-1,3-dioxol-4-yl]-carbamic acid, phenylmethyl ester.

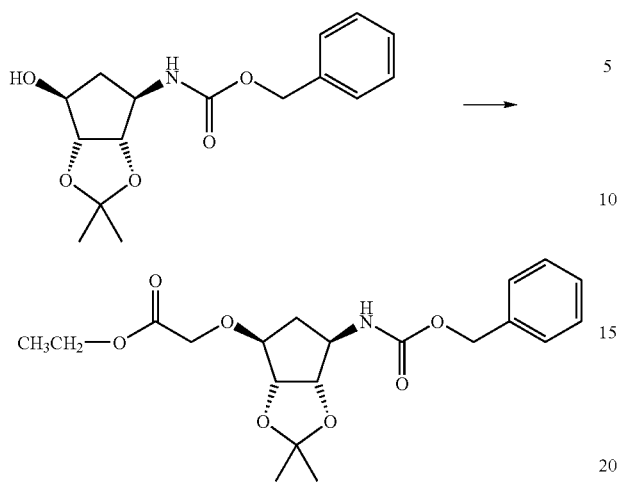

A solution (Solution A) of [3aS-(3aα,4α,6α,6aα)]-[tetrahydro-6-hydroxy-2,2-dimethyl-4H-cyclopenta-1,3-dioxol-4-yl]-carbamic acid, phenylmethyl ester (80 g, 260 mmol) in THF (160 ml), under a nitrogen atmosphere, was cooled to −22° C. A solution of potassium tert-butoxide (36.1 g, 312 mmol) in THF was prepared and added to the cooled Solution A over a period of 30 minutes, while maintaining the reaction temperature at about −20° C. This provided a reaction mixture.

A pre-made solution of ethyl bromoacetate (53.2 g, 312 mmol) in THF was then added to the reaction mixture over a period of 30 minutes while maintaining the reaction temperature at about −20° C. The resulting mixture was stirred for approximately an hour at −22° C. HPLC analysis showed that there was a 98% conversion to the desired product.

Table below shows variations on this process.

| | Mole ratios of reagents to (II) | | t-BuOK Addition | | EtBrAc Addition | | |
|---|---|---|---|---|---|---|---|
| Ex | t-BuOK | EtBrAc | Time (min.) | Temp. (° C.) | Time (min.) | Temp. (° C.) | Hold time (min.) |
| 2 | 1.40 | 1.46 | 13 | −20 | 34 | −20 | 23 |
| 3 | 1.15 | 1.15 | 22 | −22 | 42 | −22 | 20 |
| 4 | 1.20 | 1.20 | 30 | −20 | 45 | −20 | 15 |
| 5 | 1.10 | 1.10 | 20 | −30 | 30 | −30 | 20 |
| 6 | 1.20 | 1.20 | 20 | −22 | 30 | −22 | 20 |
| 7 | 1.10 | 1.10 | 20 | −10 | 30 | −10 | 20 |
| 8* | 1.20 | 1.20 | 20 | −22 | 30 | −22 | 20 |
| 9 | 1.20 | 1.20 | 30 | −22 | 180 | −22 | 150 |
| 10 | 1.20 | 1.20 | 25 | −21 | 45 | −21 | 10 |
| 11 | 1.20 | 1.20 | 30 | −22 | 40 | −20 | 10 |
| 12 | 1.2 | 1.2 | 13 | −23/−28 | 10 | −22/−28 | 30 |
| 13 | 1.15 | 1.15 | 12 | −20/−22 | 15 | −19/−24 | 30 |

Ex = Example number
(II) = [3aS-(3aα,4α,6α,6aα)]-[tetrahydro-6-hydroxy-2,2-dimethyl-4H-cyclopenta-1,3-dioxol-4-yl]-carbamic acid, phenylmethyl ester
t-BuOK = potassium tert-butoxide
EtBrAc = ethyl bromoacetate
* = Both the THF solution of compound of formula (II) and potassium tert-butoxide were filtered before use

The invention claimed is:

1. A process for the preparation of a compound of formula (I):

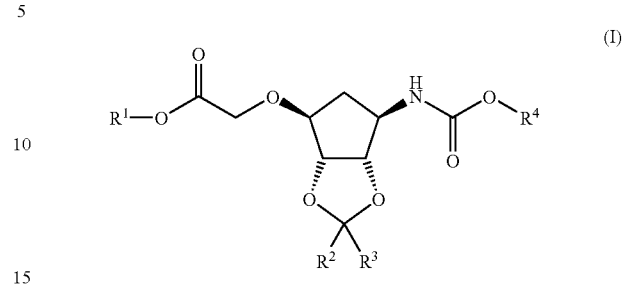

wherein
R$^1$ is C$_{1-6}$ alkyl;
R$^2$ and R$^3$ are, independently, C$_{1-6}$ alkyl; and
R$^4$ is C$_{1-6}$ alkyl or benzyl (wherein the phenyl ring of benzyl is optionally substituted by cyano, C$_{1-4}$ alkyl, C$_{1-4}$ alkoxy, CF$_3$ or OCF$_3$);
the process comprising reacting a compound of formula (II):

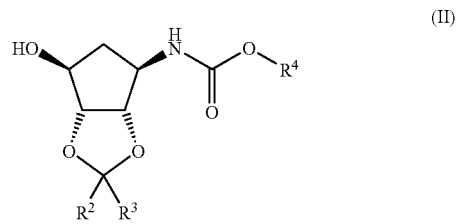

wherein R$^2$, R$^3$ and R$^4$ are as defined above, with an alkoxide base; and
reacting the product so formed with R$^1$OC(O)CH$_2$X, wherein R$^1$ is as defined above and X is chloro, bromo or iodo;
wherein the process is carried out in a suitable solvent at a temperature in the range −40° C. to −5° C.; and wherein at least 0.2 moles of the compound of formula (II) are used in the process.

2. A process as claimed in claim 1 wherein R$^1$, R$^2$ and R$^3$ are independently selected from C$_{1-4}$ alkyl.

3. A process as claimed in claim 1 wherein R$^1$ is ethyl.

4. A process as claimed in claim 1, wherein R$^2$ and R$^3$ are methyl.

5. A process as claimed in claim 1, wherein R$^4$ is benzyl optionally substituted by C$_{1-4}$ alkyl.

6. A process as claimed in claim 1, wherein R$^4$ is unsubstituted benzyl.

7. A process as claimed in claim 1 wherein X is bromo.

8. A process as claimed in claim 1 wherein the base is an alkyl metal C$_{1-6}$ alkoxide.

9. A process as claimed in claim 1 wherein the base is potassium tert-butoxide.

10. A process as claimed in claim 1 wherein the molar ratio of suitable base:R$^1$O$_2$CCH$_2$X:compound of formula (II) is (1 to 1.3):(1 to 1.3):1.

11. A process as claimed in claim 1 wherein the molar ratio of suitable base:R$^1$O$_2$CCH$_2$X:compound of formula (II) is (1.1 to 1.3):(1.1 to 1.3):1.

12. A process as claimed in claim 1 wherein the molar ratio of suitable base: $R^1O_2CCH_2X$:compound of formula (II) is 1.2:1.2:1.

13. A process as claimed in claim 1 wherein the solvent is selected from a cyclic ether, an aliphatic ether and an aromatic solvent.

14. A process as claimed in claim 1 wherein the solvent is selected from tetrahydrofuran, diethyl ether, diisopropyl ether, methyl tert-butyl ether, benzene, toluene and xylene; and a mixture of two or more of said solvents.

15. A process as claimed in claim 1 wherein the solvent is tetrahydrofuran.

16. A process as claimed in claim 1 wherein the temperature is in the range −30° C. to −10° C.

17. A process as claimed in claim 1 wherein the temperature is in the range −25° C. to −15° C.

18. A process as claimed in claim 1 wherein:
$R^1$ is ethyl;
$R^2$ and $R^3$ are methyl;
$R^4$ is unsubstituted benzyl;
X is bromo; and
the base is potassium tert-butoxide.

19. A process as claimed in claim 18 wherein the molar ratio of suitable base: $R^1O_2CCH_2X$:compound of formula (II) is 1.2:1.2:1, and wherein the solvent is selected from tetrahydrofuran, diethyl ether, diisopropyl ether, methyl tert-butyl ether, benzene, toluene and xylene, or a mixture of two or more of said solvents.

20. A process as claimed in claim 19 wherein the the temperature is in the range −25° C. to −15° C.

* * * * *